(12) United States Patent
Nebosis (10) Patent No.: US 9,036,156 B2
(45) Date of Patent: May 19, 2015

(54) SYSTEM AND METHOD FOR OPTICAL COHERENCE TOMOGRAPHY

(75) Inventor: Rainer Nebosis, Munich (DE)

(73) Assignee: Agfa HealthCare NV, Mortsel (BE)

( * ) Notice: Subject to any disclaimer, the term of this patent is extended or adjusted under 35 U.S.C. 154(b) by 34 days.

(21) Appl. No.: 14/003,562

(22) PCT Filed: Feb. 15, 2012

(86) PCT No.: PCT/EP2012/000664
§ 371 (c)(1),
(2), (4) Date: Sep. 6, 2013

(87) PCT Pub. No.: WO2012/119695
PCT Pub. Date: Sep. 13, 2012

(65) Prior Publication Data
US 2013/0342848 A1    Dec. 26, 2013

(30) Foreign Application Priority Data

Mar. 10, 2011   (EP) .................................... 11002000

(51) Int. Cl.
*G01B 11/02*      (2006.01)
*G01B 9/02*       (2006.01)
(Continued)

(52) U.S. Cl.
CPC ........ *G01B 9/02091* (2013.01); *G01N 21/4795* (2013.01); *A61B 5/0066* (2013.01); *G01B 9/02001* (2013.01)

(58) Field of Classification Search
CPC .. G01B 9/02; G01B 11/2441; G01B 21/4795; A61B 5/0066; A61B 3/102
USPC ........................................................ 356/497
See application file for complete search history.

(56) References Cited

U.S. PATENT DOCUMENTS 8,199,327 B2    6/2012   Nebosis et al.
8,330,962 B2   12/2012   Nebosis et al.
(Continued)

FOREIGN PATENT DOCUMENTS

EP        1 705 476 A1    9/2006

OTHER PUBLICATIONS

Carrion, L et al., "Comparison of Optical Coherence Tomography Profiles for Three Different Wavelengths in the Near Infrared," SPIE, vol. 5969, 2005, pp. 596922-1-596922-11.
(Continued)

*Primary Examiner* — Tarifur Chowdhury
*Assistant Examiner* — MD Rahman
(74) *Attorney, Agent, or Firm* — Keating & Bennett, LLP (57) ABSTRACT

The present invention relates to a device and a corresponding method having a light source (20) for emitting light, an interferometer (10), into which light emitted by the light source (20) is injected, for irradiating a sample (1) with light, and a, in particular spatially resolving, detector (40) for detecting interference patterns obtained by superimposing the light reflected from the sample (1) with a partial beam of the light injected into the interferometer (10) which is reflected at a reference mirror (16) of the interferometer (10).

In order to obtain OCT images in the simplest way possible and with the highest possible resolution and image quality, the light source (20) comprises a radiation source (21) for generating spatially incoherent light, and an optical filter (22) with a bell-shaped or Gaussian-shaped spectral filter characteristic for filtering the light generated by the radiation source (21).

23 Claims, 3 Drawing Sheets

(51) Int. Cl.
*G01N 21/47* (2006.01)
*A61B 5/00* (2006.01)

(56) References Cited

U.S. PATENT DOCUMENTS

| | | | |
|---|---|---|---|
| 8,339,610 B2 | 12/2012 | Nebosis et al. | |
| 8,526,006 B2 | 9/2013 | Nebosis et al. | |
| 2003/0142222 A1* | 7/2003 | Hordley | 348/223.1 |
| 2010/0027020 A1 | 2/2010 | Nebosis | |
| 2010/0033726 A1 | 2/2010 | Nebosis et al. | |
| 2010/0067022 A1 | 3/2010 | Nebosis et al. | |
| 2010/0091295 A1* | 4/2010 | Nebosis et al. | 356/496 |
| 2010/0149543 A1* | 6/2010 | Nebosis | 356/450 |
| 2010/0284016 A1* | 11/2010 | Teitell et al. | 356/451 |

OTHER PUBLICATIONS

Choi, ES., "Fiber-based High Resolution OCT System with Halogen Light Source," SPIE, vol. 5316, 2004, pp. 454-462.
Akcay, A.C. et al., "Spectral shaping to improve the point spread function in optical coherence tomography," Optical Society of America, Optic Letters, vol. 28, No. 20 2003, pp. 1921-1923.
International Search Report dated May 4, 2012, from International Application No. PCT/EP2012/000664 filed on Feb. 15, 2012.
European Search Report, completed on Jun. 22, 2011, from European Application Publication No. EP 11 00 2000.
International Preliminary Report on Patentability and the Written Opinion of the International Searching Authority issued Sep. 10, 2013, from counterpart International Application No. PCT/EP2012/000664, filed on Feb. 15, 2012.

* cited by examiner

SYSTEM AND METHOD FOR OPTICAL COHERENCE TOMOGRAPHY

The present invention relates to a system and a corresponding method for optical coherence tomography according to the preamble of the independent claims.

Optical coherence tomography (OCT) is a method of measuring light-scattering specimens on their inside. Due to its light-scattering properties biological tissue is particularly suitable for diagnostic examination by means of OCT. Since for OCT relatively low light intensities are sufficient and the wavelengths of the light used mostly come within the near infrared range (750 nm to 1350 nm), unlike ionising X-ray diagnostics it does not contaminate biological tissue with radiation. It is therefore particularly significant for medicine and is roughly comparable to ultrasound diagnostics, wherein with OCT, light is used instead of sound. The running times of the light reflected on different boundary layers within the specimen are recorded with the aid of an interferometer. With OCT, typically resolutions higher by one to two orders of magnitude are to be achieved than with ultrasound, but the measuring depth achievable is considerably smaller. Due to optical scattering the cross-section images obtained only reach into the tissue up to a depth of a few millimeters. The currently most important areas of application of OCT are in ophthalmology, dermatology and the diagnosis of cancer. However, there are also some non-medical applications, such as e.g. in materials testing.

In OCT systems light sources with high spatial and temporal coherence are often used, such as superluminescent diodes (SLDs). As a general rule however, the light from such light sources allows only a low depth resolution. In addition, when a spatially resolving area detector is used at the same time, so-called ghost images can occur due to coherent crosstalk, which could only be avoided by an almost complete destruction of the spatial coherence. This latter is something which on the one hand requires a certain level of technical complexity and, on the other hand, despite the technical complexity, is only possible under certain conditions. In addition, if the light from a plurality of different SLDs is superimposed to form a light source, ghost images can be caused due to secondary maxima in the spectrum. In addition, because of their relatively low power of up to approximately 20 mW, which also decreases with increasing spectral bandwidth, the use of SLDs is not always able to deliver a signal-to-noise ratio which is adequate for high image quality.

It is the object of the present invention to specify a system and a corresponding method for optical coherence tomography with which OCT images with the highest possible resolution and image quality can be obtained as simply as possible.

This object is achieved by the system or method, respectively, in accordance with the independent claims.

The system according to the invention comprises a light source for emitting light, an interferometer, into which light emitted by the light source is injected and with which a sample can be irradiated with light, and a detector, in particular a spatially resolving detector, for detecting light which is reflected by the sample. The light source is composed of a radiation source for generating spatially incoherent light and an optical filter with a bell-shaped or Gaussian spectral filter characteristic for filtering the light generated by the radiation source.

In the method according to the invention, light emitted by a light source is injected into an interferometer, a sample is irradiated with light which is emitted by the interferometer, and light reflected from the sample is detected with a, in particular, spatially resolving detector, wherein the light emitted by the light source is obtained by filtering spatially incoherent light, which is generated by a radiation source, with an optical filter having a bell-shaped or Gaussian spectral filter characteristic.

Detection of the light reflected from the sample by the detector means that the detector detects interference patterns which are obtained by superposition of the light reflected from the sample with a partial beam of the light injected into the interferometer, which is reflected at a reference mirror of the interferometer. The superposition in this case is effected at a beam splitter of the interferometer.

Within the context of the invention the term spatially incoherent light is to be understood as meaning electromagnetic radiation, the partial waves of which have no fixed spatial phase relationships to one another or have only a very small coherence length. The coherence length in this case is a distance which the partial waves travel before their phase or amplitude relative to each other has changed significantly, and is defined in particular as the point at which the degree of coherence has dropped to 1/e. The degree of coherence can be derived from the contrast of the interference pattern received in each case (a high contrast, i.e. large difference between interference maxima and minima, corresponds to a high degree of coherence). A very small coherence length within the context of the invention applies in particular if the coherence length of the electromagnetic radiation generated by the radiation source is less than 15 μm, and in particular only a few microns.

A Gaussian-shaped spectral filter characteristic within the context of the invention is to be understood to mean that the transmittance of the optical filter for light with particular wavelengths $\lambda$ is proportional to $\exp[-[(\lambda-\lambda_0)/2 \cdot \Delta\lambda]^2]$, where $\lambda_0$ designates the wavelength at which the optical filter has its maximum transmittance, and $\Delta\lambda$ the standard deviation, which is related to the full width at half maximum (FWHM) of the Gaussian transmittance curve as follows: $FWHM \approx 2.35 \cdot \Delta\lambda$.

A bell-shaped spectral filter characteristic is to be understood as a spectral plot of the transmittance of the optical filter, which can be approximated by a Gaussian function and/or only deviates from a Gaussian function to the extent that its Fourier transform has essentially a Gaussian shape with either no or only a small number of very low secondary maxima, the height of which is a maximum of 5% of the maximum of the Fourier transform.

The invention is based on the idea of coupling light into the interferometer, which is obtained by optical filtering of the spatially incoherent light produced by a radiation source by means of a bell-shaped or Gaussian filter.

Due to the use of a radiation source, which a priori generates spatially incoherent light, in the detection of the light reflected by the sample by means of a two-dimensional spatially resolving detector the occurrence of so-called ghost images caused by coherent crosstalk between light beams from different locations within the sample under test is prevented. The additional equipment for destroying the spatial coherence, which is normally required when using spatially coherent radiation sources, can thereby be omitted.

In addition, in the system or method, respectively, according to the invention, thermal radiation sources such as incandescent or halogen lamps can be used to produce incoherent light, which are much more powerful and more cost-effective than the frequently used superluminescent diodes (SLDs).

Due to the optical filtering with a Gaussian or bell-shaped filter characteristic, the light generated by the radiation source is converted into temporally partially coherent light with a temporal coherence length of preferably more than approximately 6 μm. This is particularly advantageous with the system according to the invention which is of the so-called time-domain OCT type, in which the length of a reference arm in the interferometer changes and the intensity of the resulting interference is continuously detected by means of a preferably two-dimensional detector because, by filtering the light using the bandpass realized by the optical filter on the one hand, a high lateral resolution of the image captured from the sample is obtained, and on the other hand, due to the Gaussian or bell-shaped spectral filter characteristic of the optical filter, the occurrence of interfering secondary maxima in the Fourier transform of the interference pattern detected by the detector, which would cause the occurrence of further ghost images, is avoided.

Overall, with the system or method, respectively, according to the invention, OCT images with high resolution and image quality are easily obtained.

In a first preferred embodiment the optical filter has a maximum transmittance for light in a spectral range between approximately 1200 nm and 1400 nm, in particular between about 1270 nm and 1330 nm. In the case of a Gaussian curve proportional to $\exp[-[(\lambda-\lambda_0)/2\cdot\Delta\lambda]^2$, the wavelength $\lambda_0$ lies in the above-mentioned spectral range. The result obtained is that the spectrum of the light injected into the interferometer has an intensity maximum in the above-mentioned spectral range, which in the radiation treatment of biological tissue in particular, is absorbed and/or scattered less strongly by the sample than light in other spectral ranges. A relatively high penetration depth is thereby achieved.

Preferably, the optical filter has a full width at half maximum (FWHM≈2.35·Δλ) which is less than 250 nm. The full width at half maximum (FWHM) is to be understood as the spectral width at a transmittance corresponding to half the maximum transmittance of the filter. With this full width at half maximum (FWHM) of the optical filter, in the system according to the invention of the time-domain OCT type, a particularly high lateral resolution of the images obtained from the sample is achieved.

In a preferred embodiment, the spatially incoherent light produced by the radiation source has a spectrum with a bandwidth of at least 500 nm. This ensures that the light generated by the radiation source is incoherent, or has a sufficiently small coherence length of preferably less than 15 μm. The occurrence of ghost images in the two-dimensional spatially resolved detection of the light reflected by a flat area of the sample is thereby prevented with particularly high reliability.

Preferably, the light generated by the radiation source has a continuous spectrum. The result of this is that, even after the filtering by the optical filter, in the transmittance range of the filter the light has a continuous spectrum with a substantially smooth shape, in particular without interruptions, discontinuities or the like. Accordingly, in the Fourier transform of the interference patterns captured by the detector, either no or only very weak secondary maxima occur, which facilitates a particularly reliable evaluation of the interference patterns.

It is particularly advantageous if the light generated by the radiation source, in particular in the transmittance range of the optical filter, has a spectrum without spectral lines, in particular without spectral emission lines and/or absorption lines. This also contributes to ensuring that unwanted components in the Fourier transform of the interference patterns captured by the detector are greatly reduced or even prevented.

It is particularly preferred that the light generated by the radiation source has a spectrum in the form of a Planck radiator, in particular a black or grey body. A Planck radiator or a black body is to be understood to mean a thermal radiation source which emits electromagnetic radiation with a continuous, characteristic spectrum that is dependent only on the temperature of the radiator. A grey body has a spectrum which corresponds to the spectrum of the black body multiplied by a factor less than 1. The factor corresponds to the emissivity of the grey body. A Planck radiator within the context of the invention, however, is also a radiator whose emission spectrum can be approximated by the spectral shape of a Planck radiator.

Preferably, the radiation source has a colour temperature located between approximately 2500 K and 3200 K, in particular between about 2700 K and 3000 K. The colour temperature is a reference value which characterizes the intensity curve of a black body according to Planck's radiation law and Wien's displacement law. That is to say, the radiation source generates light whose spectral composition corresponds to that of a black or grey body with this (colour) temperature. The choice of the colour temperature of the radiation source in the range mentioned ensures that the generated light has a spectrum which has a relatively flat descent in the spectral range which is particularly favourable for the examination of biological tissue, in particular between about 1000 nm and 1500 nm. In particular, the mean gradient of the curve in this spectral range is considerably smaller than in other spectral ranges.

It is preferred moreover that the light generated by the radiation source has a spectrum which, in the spectral range under consideration, has at most one maximum intensity value. Another result obtained in these embodiments is that after filtering by the optical filter, the light has a spectrum with a substantially smooth shape, in particular one without interruptions, discontinuities or the like, and approximately the shape of a Gaussian curve. Therefore, under a Fourier transform of the interference patterns captured by the detector, either no or at most weak secondary maxima occur, which allows a reliable evaluation of the detected interference patterns and guarantees a high quality of the image derived therefrom.

Advantageously, the light generated by the radiation source in the spectral range considered has a spectrum with a largest and a smallest intensity value, whereby the difference between the largest and the smallest intensity value is no more than 25%, in particular no more than 10%, of the largest intensity value. Alternatively or in addition, the light generated by the radiation source in the spectral range considered has a spectral power density, i.e. an intensity curve, which is only slightly dependent on the wavelength or is independent of the wavelength. The choice of a corresponding radiation source, or of the spectral range of the radiation source under consideration, ensures that the light generated has a spectrum with only limited maximum intensity differences in the respective spectral range, which means that after filtering the light by the optical filter a relatively smooth and essentially Gaussian or bell-shaped intensity curve is obtained, so that another result of this measure is that an occurrence of interfering secondary maxima can be selectively reduced or even suppressed in the evaluation of the detected interference patterns.

In the above embodiments, the spectral range considered is preferably between about 1000 nm and 1600 nm and has a bandwidth of at least 500 nm. Alternatively or in addition, the spectral range considered corresponds to the spectral range in which the optical filter transmits light. Alternatively or in addition, the spectral range in which the optical filter has a maximum transmittance for light, in the spectral range considered. The above mentioned advantages thus become particularly efficacious.

It is particularly preferred that the light emitted by the light source has a spectrum whose Fourier transform has a maximum and possibly one or more secondary maxima, the height of which is less than 5%, in particular less than 1%, of the size of the maximum. In this embodiment it is ensured that any secondary maxima that may occur in the evaluation of the detected interference patterns are only very weakly distinctive and therefore affect the evaluation only marginally or not at all.

In a further preferred embodiment, the light generated by the radiation source is irradiated via a first area, the size of which is of the same order of magnitude as the size of a second area of the sample which is irradiated by the light emitted by the interferometer. This means that the light-emitting area of the radiation source is approximately the same size as—and in particular not substantially smaller than—the area on the sample being examined and irradiated with light from the interferometer. Alternatively or in addition, this applies accordingly to the solid angular range into which the light generated by the radiation source is emitted in the direction of the optical filter and the interferometer, or in which the light emitted by the interferometer is radiated in the direction of the sample. The relatively large-area structure of the light-emitting area and/or of the corresponding solid angle of the radiation source in relation to the illuminated area of the sample ensures that the spatially incoherent light generated by the radiation source retains its spatial incoherence, which due to the so-called "van Cittert-Zernike theorem" would not be the case for relatively small light-emitting areas, such as virtually point-shaped light sources or small size light sources such as SLDs. This advantage also becomes important with light generated by the radiation source with a very small coherence length, in particular of less than 15 μm. The advantages already mentioned above in connection with the use according to the invention of spatially incoherent light, or light with a very short coherence length, are achieved by these measures with a very high reliability.

It is preferred in this regard that the sizes of the first and second area differ by no more than 20%, in particular by no more than 10%. Alternatively or in addition it can be provided that the size of the first and/or second area is at least $0.25\, mm^2$, preferably at least $1\, mm^2$. These measures also contribute to obtaining the above advantages due to the use of incoherent light, or of light with a very low coherence length, in a reliable and particularly simple manner.

It is also advantageous if the light generated by the radiation source is irradiated via a first area with an essentially constant intensity. This will, on the one hand, further contribute to the fact that the irradiated light of the radiation source retains its spatial incoherence, and, on the other hand, guarantees a uniform illumination of the illuminated area on the sample.

An essential aspect of the OCT system according to the invention therefore relates to the limitation of the bandwidth of a broadband radiation source using a Gaussian or bell-shaped optical filter. In addition to the advantages already described in detail above, the following advantages have also been obtained, or problems solved as the case may be.

Without any filtering according to the invention of the light produced by the radiation source, at the optical surfaces located between the light source and the detector (typically more than ten surfaces due to lenses, filters, optical fibre facettes, beam splitter etc.) with anti-reflex coatings, this light would be transmitted to varying degrees depending on the wavelength, and in addition would also impinge on these surfaces at different angles, causing an overall adverse effect on the homogeneity of the transmission over a large spectral range. As a result, the spectrum of the light would change depending on the position in the beam path, and would therefore be undefined. This applies in particular to light sources with large bandwidth (FWHM greater than 300 nm), since the anti-reflex coating cannot have a uniform transmittance for bandwidths of any size. Corresponding losses in image quality would occur as a result. Due to the filtering according to the invention of the incoherent light generated by the radiation source, the occurrence of these disadvantages is avoided.

Without the filtering according to the invention of the incoherent light generated by the radiation source, or in the case of an extremely broadband light source, the light injected into the interferometer would have extremely short temporal coherence lengths (here meaning the coherence length along the propagation axis of the light, in contrast to the spatial coherence length), so that the so-called coherence gate would be shorter than the mean wavelength of the light injected into the interferometer. The coherence gate is designated as the distance between two planes or points within the sample within which there is a constant phase relationship, so that interference can occur.

Certain algorithms for analyzing interference patterns would therefore no longer be applicable. In contrast, the invention allows the use of a digital demodulation algorithm, in which an interference pattern is sampled with five points at a distance of Tc/2 apart, without the so-called sampling theorem being violated.

In addition, the modulation of the light intensity or detector sensitivity, as described in more detail below, in order to increase the depth scan speed when the bandwidth of the light source is too large, would not lead to the desired result. This is true in particular if the above-described demodulation algorithm is used in this context, in which it is not the interference itself but a beating between interference and a second signal that is sampled. Since the beating has a longer wavelength (at least by a factor of 3), a coherence length is required which is greater than 3.2 times the mean wavelength of the light injected into the interferometer. For a mean wavelength of about 1300 nm, this means that the coherence length would have to be greater than about 4 μm. This can be achieved by appropriate choice of the bandwidth of the optical filter with a Gaussian or bell-shaped spectral characteristic.

Further advantages, features and possible applications of the present invention are shown in the following description in connection with the figures.

Figure 1:
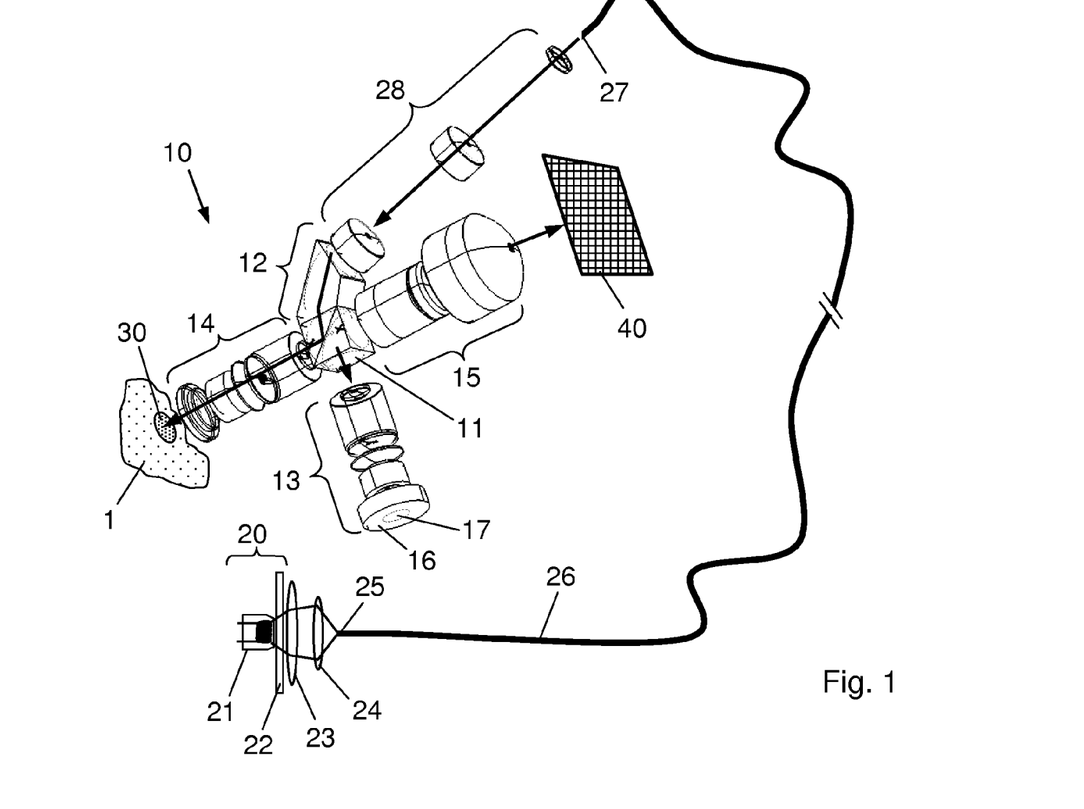
FIG. 1 shows a schematic representation of a system for optical coherence tomography.

FIG. 1 shows a schematic representation of a system for optical coherence tomography with an interferometer 10, which comprises a beam splitter 11, an illumination arm 12, a reference arm 13, a sample arm 14, and a detector arm 15. In addition, a radiation source 21 is provided for generating light, which is filtered by an optical filter 22 and is focused through optics composed of lenses 23 and 24 onto an input region 25 of an optical waveguide 26. The radiation source 21, together with the optical filter 22, forms a device which in the context of the present invention is designated as light source 20.

The light from the radiation source 20 that is injected into the optical waveguide 26 by means of the lenses 23 and 24 is injected into the illumination arm 12 of the interferometer 10 by means of optics 28 located in the output region 27 thereof. From there, the injected light first reaches the beam splitter 11, through which it is forwarded into the reference arm 13 and reflected by a movable reference mirror 16 located at the end thereof and, after passing through the sample arm 14, illuminates an area 30 of a sample 1.

The light reflected from the sample 1 passes through the sample arm 14 once more, is superimposed in the beam splitter 11 with the light from the reference arm 13 reflected at the reference mirror 16, and finally arrives via the detector arm 15 at a detector 40, which comprises a plurality of detector elements arranged in a, preferably flat, surface and as a consequence, facilitates a spatially resolved detection of the light reflected from the sample 30 or of a corresponding interference pattern due to the superposition thereof with the light reflected at the reference mirror 16.

A CMOS camera is preferably used as the detector 40, the detector elements (so-called pixels) of which are sensitive in the infrared spectral range, in particular in a spectral range between approximately 1250 nm and 1350 nm. Preferably, the CMOS-camera has 512×640 detector elements.

As the waveguide 26 a so-called multimode fibre is preferably used, the numerical aperture and core diameter of which, for a specific wavelength of light injected into the fibre, allow not just one fibre mode to be formed but many different fibre modes to be excited. Preferably, the diameter of the multimode fibre used is between approximately 1 mm and 3 mm, and in particular approximately 1.5 mm.

The size of the illuminated area 30 on the sample 1 corresponds approximately to the size of the illuminated area 17 on the reference mirror 16. The size of the illuminated area 30 on the sample 1 is defined firstly by the optics situated at the input region of the optical waveguide 26, which in the example shown comprises the lenses 23 and 24, and secondly via the optics 28 arranged in the output region of the optical waveguide.

In the described system, the resulting interference pattern is detected with the detector 40, wherein a corresponding interference signal is generated. The sampling rate of the detector 40 for sampling the interference signal must be selected such that the temporal variation of the interference pattern can be detected with sufficient accuracy. In general this requires high sampling rates, if high speeds are to be achieved for a depth scan.

A depth scan is preferably realized in the system described by causing the optical distance from the reference mirror 16 to the beam splitter 11 to be changed with a speed v during the detection of the light reflected from the sample 1 with the detector 40, by an optical path length which is substantially larger than the mean wavelength of the light injected into the interferometer 10. Preferably, the light reflected in at least 100 different depths of the sample 1 is captured by the detector 40. In particular, it is preferred that the optical path is changed periodically with an amplitude which is substantially larger than the mean wavelength of the light injected into the interferometer 10. The change of the optical distance of the reference mirror 16 by the optical path or the amplitude respectively, is preferably at least 100 times, in particular at least 1000 times, greater than the mean wavelength of the light injected into the interferometer 10.

Since the individual periods of an interference pattern in general need to be sampled at multiple time points respectively, the maximum possible scanning speed in the direction of the depth of the sample 1 is dependent on the maximum possible sampling rate of the detector 40. When using fast detector arrays with high spatial resolution, i.e. a large number of detector elements per unit length, the maximum sample rate is typically in the range of approximately 1 kHz. For a mean wavelength of the light injected into the interferometer of, for example, 1300 nm, this will result in a maximum speed for the depth scan of approximately 0.1 mm/s, if four points per period of the interference structure are sampled.

To increase the speed of the depth scan, in the present OCT system the temporal profile of the sensitivity of the detector 40 for the light to be detected is modulated with a frequency that is up to 40% greater than or less than the Doppler frequency $f_D$, wherein the Doppler frequency $f_D$ is related to the mean wavelength $\lambda_0$, of the light injected into the interferometer 10 and the speed v of the moving reference mirror 16 as follows: $f_D=2v/\lambda_0$. Typical frequencies of this modulation are in the range between 1 kHz and 25 kHz. It is particularly preferable that the frequency of the modulation of the detector sensitivity is not equal to the Doppler frequency $f_D$.

The light reflected by the sample 1 and impinging on the detector 40 is superimposed with the modulated sensitivity of the detector 40, so that during the detection of the interference pattern impinging on the detector 40, instead of a high-frequency interference signal with a plurality of periods, the detector 40 generates a low-frequency beat signal which has markedly fewer periods than the high-frequency interference signal. In sampling this beating, considerably fewer sampling time points per time unit are therefore necessary, without losing any relevant information, than for sampling of the high-frequency interference signal without the modulation of the sensitivity of the detector 40. For a given maximum sampling rate of the detector 40, this means that the maximum speed for a depth scan of the system can be increased many times.

The sensitivity of the detector 40 can be modulated, e.g. directly or with a controllable electronic shutter arranged in front of the detector 40. As an alternative or in addition, properties of an optical element in front of the detector 40, such as e.g. the transmittance of a detector lens 1 for the light reflected from the sample 1, can be modulated. Compared to systems with a constant detector sensitivity this increases the scanning speed by a factor of 4 or even 8.

The speed of the movement of the reference mirror 16 is in a fixed relationship to the frequency of the modulation of the sensitivity of the detector 40 and is preferably chosen such that an integral number of sampling time points, preferably four sampling time points, fit into one period of the resulting beating signal.

The beating signals sampled in this way need to be further processed prior to being displayed, since these signals still contain the interference information. The essential information to be displayed is the amplitude and depth position of the respective interference, but not the interference structure itself. In order to do this the beating signal must be demodulated, by determining the so-called envelope of the beating signal by Fourier transformation.

Since the phase of the beating signal is in general unknown, and this can also differ for different beating signals from different depths, a digital demodulation algorithm is used, which is independent of the phase. For sampling the interference signal with four sampling time points per period, the so-called 90° phase shift algorithms are preferably used. This allows a fast demodulation of the beating signal to be obtained.

Preferably, one period of the modulation of the sensitivity of the detector 40 comprises two sub-periods, wherein during a first sub-period the detector is sensitive and during a second sub-period the detector is insensitive to the light to be detected. In general, the first and the second sub-period are equal in length. However, it can be advantageous to choose a different duration for the first and second sub-period. This is the case, for example, when the intensity of the light emitted by the light source 20, or injected into the interferometer 10, and/or of the light reflected from the sample 1, is relatively low. In these cases the first sub-period can be selected such that its duration is longer than the duration of the second sub-period. In this way, even at low light intensities, in addition to a high depth scanning speed a high signal-to-noise ratio, and thus a high image quality, is ensured.

Alternatively, the intensity of the light injected into the interferometer 10 can also be temporally modulated, wherein the remarks on the modulation of the detector sensitivity described above, including the advantages, apply accordingly.

Figure 2:
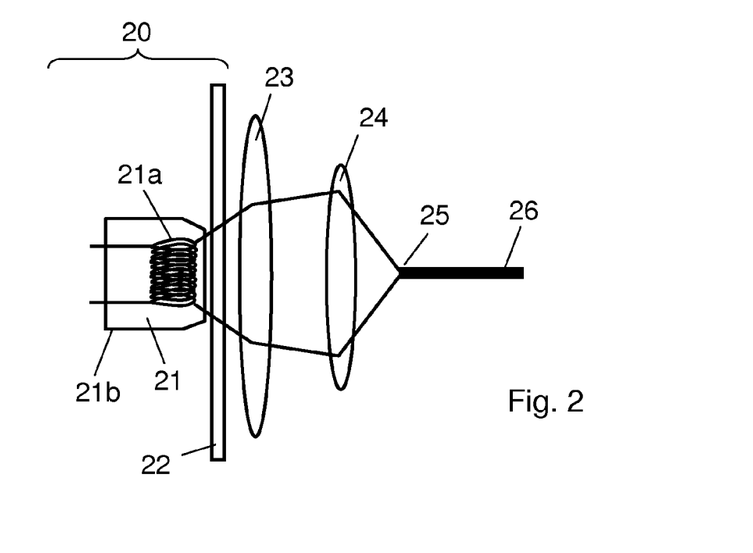
FIG. 2 shows a section of the system shown in FIG. 1.

FIG. 2 shows a section of the system shown in FIG. 1 at the input region 25 of the optical waveguide 26. As shown in the figure, the radiation source 21 includes a spiral-shaped wire 21a, which is surrounded by a transparent casing 21b, preferably made of glass. Preferably, the radiation source 21 is implemented as a halogen light bulb, in particular a tungsten halogen bulb, where a tungsten filament is used as the wire 21a and the inside of the casing 21b is filled with gas, which contains a halogen, such as iodine or bromine. By application of an electrical voltage, the spiral wire 21a is made to glow, which causes it to emit spatially incoherent light. The term spatially incoherent light within the context of the present invention is to be understood as light whose spatial coherence length is less than 15 µm, and in particular only a few µm, i.e. between approximately 1 µm and 5 µm.

The spatially incoherent light generated by the radiation source 21 passes through the optical filter 22, which is implemented as a band-pass filter and essentially only transmits light within a specifiable spectral bandwidth. The optical filter 22 has a bell-shaped or Gaussian spectral filter characteristic, wherein only those spectral light components of the light generated by the radiation source 21 which lie within the specified bandwidth about a mean wavelength of the bell-shaped or Gaussian spectral filter characteristic can pass through the optical filter 22.

In the example shown, the optical filter 22 is arranged between the radiation source 21 and the optics formed from the two lenses 23 and 24 on the input side. In principle, it is also possible however to provide the optical filter 22 between the two lenses 23 and 24 or between the lens 24 and the input region 25 of the optical waveguide 26. Essentially, an arrangement of the optical filter 22 is particularly advantageous if the light rays impinging on the optical filter 22 have only a small divergence, or in particular run parallel to one another, because, firstly, this reduces reflection losses at the boundary surfaces of the optical filter 22 and secondly, it prevents any beam displacement due to light refraction. In the example shown therefore, an arrangement of the optical filter 22 between the two lenses 23 and 24 of the optics is preferred.

Alternatively or in addition, it is also possible to mount the optical filter 22 directly on the casing 21b of the radiation source 21. This has the advantage that an additional filter component can be dispensed with.

Alternatively or in addition, it is also possible to arrange the optical filter 22 between the output region 27 of the optical waveguide 26 and the illumination arm 12, for example in front of or between the lenses of the optics 28 located between the output region 27 of the optical waveguide 26 and the input of the illumination arm 12.

In a simple and highly reliable variant the optical filter 22 comprises an absorption filter, in particular a so-called dyed-in-the-mass glass, and an interference filter, wherein multiple, preferably between about 30 and 70, thin layers with different refractive indices are applied to the dyed-in-the-mass glass, for example, by vapour deposition, which results in an interference filter.

For the case where the optical filter 22 is integrated into the casing 21b of the radiation source 21, the optical filter 22 is preferably implemented by applying such interference layers to the casing 21b. As an alternative, or in addition, it is also possible however to provide one or more of the lenses 23, 24 or the lenses of the optics 28 with a corresponding interference filter.

Figure 3:
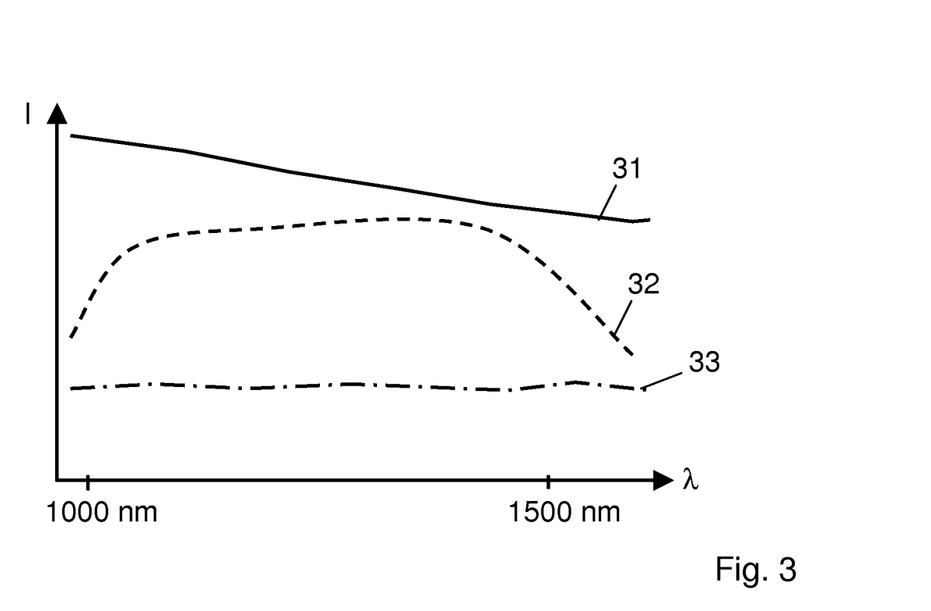
FIG. 3 shows examples of the spectral composition of the light generated by the radiation source.

FIG. 3 shows examples for the spectral composition of the light generated by the radiation source 21, where in the present case the spectral intensity I is plotted against the wavelength λ.

The first curve 31 shown in FIG. 3 corresponds to a portion of the total spectrum of a Planck radiator, in particular a black or grey body with a colour temperature of approximately 3000 K. In this case the spectral range considered is located at a wavelength λ between approximately 1000 nm and 1500 nm. The first curve 31 in this spectral range already shows a relatively flat descent, so that the difference between the intensity I at a wavelength λ of 1000 nm and the intensity I at a wavelength of approximately 1500 nm is only equal to around 20% of the intensity at a wavelength of 1000 nm.

FIG. 3 also shows a second spectral curve 32 of the light produced by the radiation source 21, which indeed falls off more steeply in the region of the upper and lower limits of the spectral range under consideration between 1000 Nm and 1500 nm, but in between these areas is relatively flat and therefore is particularly suited to the present system.

In addition, FIG. 3 shows an example of a third spectral curve 33 of the light emitted by the light source 21. In this case, the curve is particularly flat in the spectral range under consideration between approximately 1000 nm and 1500 nm, so that the difference between the maximum and the minimum intensity value in the relevant spectral range is only a few per cent.

Common to the curves 31, 32 and 33 shown in FIG. 3 is the fact that in the spectral range considered each of these shows a continuous spectrum which has no discontinuities, for example due to strong absorption bands or the like. In addition, the spectra shown in FIG. 3 have no spectral emission lines, such as occur in the spectrum of Xenon lamps, and they also show furthermore a substantially smooth shape in the spectral range considered between 1000 nm and 1500 nm without major variations in spectral intensity.

Figure 4:
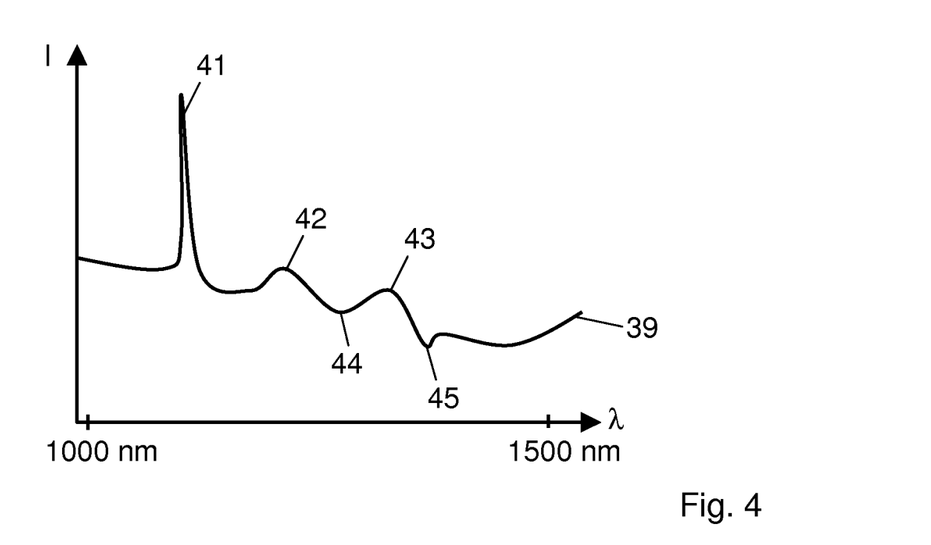
FIG. 4 shows a comparative example to the examples shown in FIG. 3.

For comparison with the examples of spectral characteristics of preferred radiation sources 21 shown in FIG. 3, FIG. 4 shows an example of a spectral curve 39 of the light from a radiation source, which in the spectral range considered between approximately 1000 nm and 1500 nm displays a clearly visible spectral emission line 41 and in addition, a strong dependence of the spectral intensity I on the respective wavelength λ. The latter is illustrated by the peaks 42 and 43 and valleys 44 and 45 shown in the figure.

Figure 5:
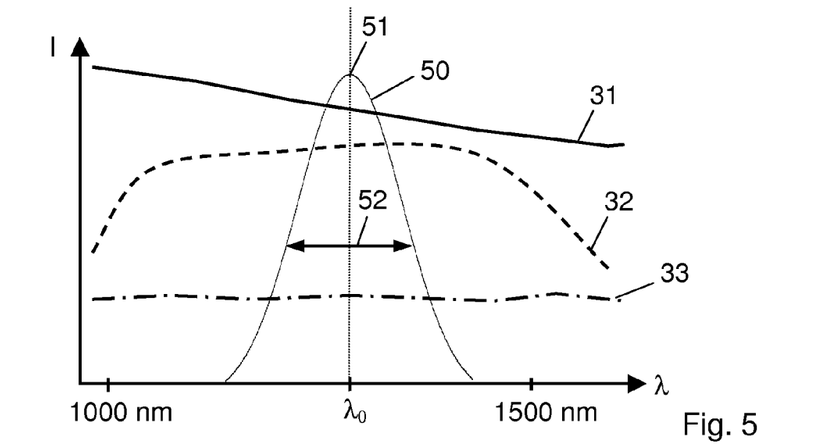
FIG. 5 shows an example of the spectral filter characteristic of the optical filter in conjunction with the examples shown in FIG. 3 for the spectral composition of the light generated by the radiation source.

FIG. 5 shows an example of a spectral filter characteristic 50 of the optical filter 22 together with the examples shown in FIG. 3 for the spectral curves 31, 32 and 33 of the light generated by the radiation source 21. The spectral filter characteristic 50 shown in the Figure has a bell-shaped or Gaussian curve, whose maximum 51 lies in a spectral range between approximately 1200 nm and 1400 nm, preferably between about 1280 nm and about 1320 nm, and has a full width at half maximum (FWHM) 52 of less than about 250 nm.

By the filtering according to the invention of the light produced by the radiation source 21 with a—in relation to the full width at half maximum (FWHM) 52 of the spectral filter characteristic 50 of the optical filter 22 of preferably less than 250 nm—relatively broad spectral range, with a width of more than approximately 400 nm, and with a relatively smooth and flat spectral curve (see the example curves 31, 32 and 33 shown), light is obtained, the spectrum of which also essentially has a bell-shaped or Gaussian curve.

This has the particular advantage that the Fourier transform of the light obtained in this way has only a few secondary maxima, the height of these being substantially less than that of the maximum of the Fourier transform.

Figure 6:
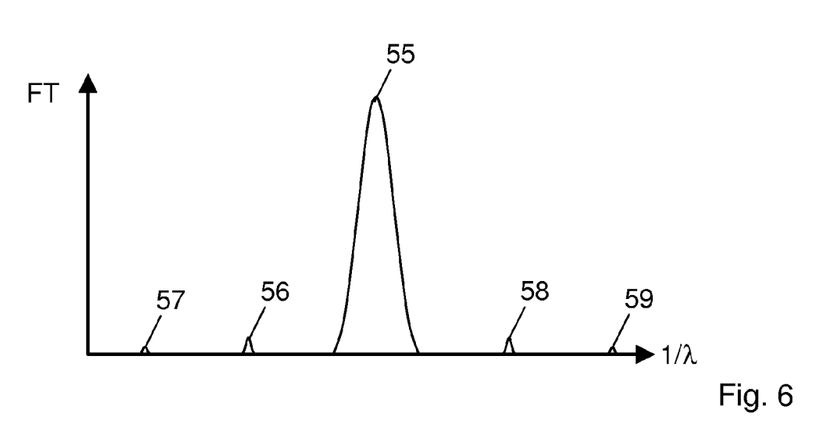
FIG. 6 shows an example of a Fourier transform of the light from the light source.

This is illustrated in FIG. 6, in which the Fourier transform FT of the light emitted by the light source 20, i.e. the light generated by the radiation source 21 and filtered by the optical filter 22, is shown schematically. In the example shown in FIG. 6, the Fourier transform FT has a maximum 55 and a total of four secondary maxima, namely two first-order secondary maxima 56 and 58 and two second-order secondary maxima 57 and 59. As can be seen, the height of the respective secondary maxima 56 to 59 is very small relative to the maximum 55.

Preferably, the height of the secondary maxima 56 to 59 is no more than 5%, in particular less than 1% of the height of the maximum 55. This means that the occurrence of ghost images in the detection of the light reflected by the sample 1 and passing through the interferometer 10 is greatly reduced or even eliminated by means of the detector 40. A further contributory factor here is the fact that the light generated by the radiation source 21 is spatially incoherent, which prevents so-called crosstalk of light rays from different lateral positions in the sample 1, which otherwise, if the light reflected by the sample 1 were detected using a two-dimensional spatially resolving detector 40, would also lead to ghost images.

Figure 7:
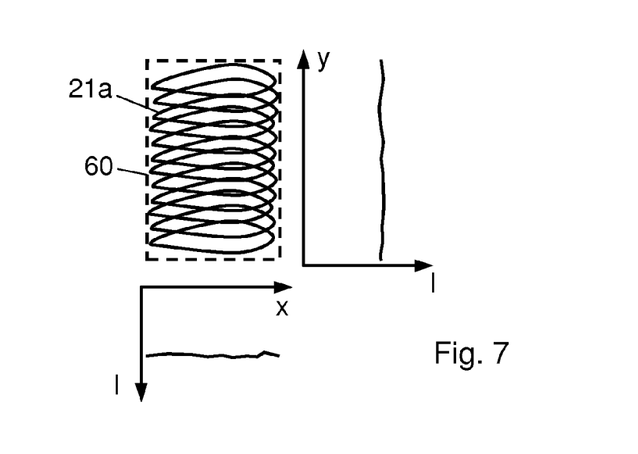
FIG. 7 shows a section of the radiation source shown in FIG. 2.

FIG. 7 shows a section of the filament 21a of the radiation source 21 shown in FIG. 2, in the region of the spiral-shaped path. The spiral-shaped filament 21a of the radiation source 21 emits light in the direction of the optics formed by the two lenses 23 and 24 (see FIG. 2) and of the input region of the optical waveguide 26, wherein the region of the spiral-shaped path can be considered as a first area 60, through which the light generated by the filament 21a is emitted in the direction of the optical fibre 26.

As can be seen from the diagrams shown in FIG. 7 at the sides of the first area 60, the intensity I of the light from the filament 21a passing through the first area 60 in both dimensions x and y of the first surface 60 is essentially constant.

The size of the first area 60 is at least approximately 0.25 mm$^2$, preferably at least 1 mm$^2$, and has the same order of magnitude as the size of the illuminated second area 30 on the sample 1 (see FIG. 1). With this size range of the first area 60 or this size ratio of the first area 60 to the second area 30, the spatial incoherence of the light produced by the radiation source 21 is preserved, which for relatively small radiation sources such as, for example virtually point-shaped light sources or small size light sources such as SLDs, would not be the case. The advantages achieved by the use according to the invention of spatially incoherent light, or light with a very short coherence length, are obtained with a particularly high reliability by these measures.

The invention claimed is:

1. A system for optical coherence tomography, the system comprising:
   a light source configured to emit light;
   an interferometer, into which the light emitted by the light source is injected, configured to irradiate a sample with light; and
   a detector configured to detect light reflected from the sample; wherein
   the light source includes a radiation source configured to generate spatially incoherent light and an optical filter having a bell-shaped or Gaussian-shaped spectral filter characteristic configured to filter the light generated by the radiation source;
   the filtered light emitted by the light source has a spectrum, a Fourier transform of which has a maximum and one or more secondary maxima a height of which is less than 5% of a height of the maximum; and
   the light generated by the radiation source has a spectrum with a maximum intensity value and a minimum intensity value, and a difference between the maximum intensity value and the minimum intensity value in a relevant spectral range corresponds to at most 25% of the maximum intensity value.

2. The system according to claim 1, wherein the optical filter has a maximum transmittance of light which lies in a spectral range between approximately 1200 nm and 1400 nm.

3. The system according to claim 1, wherein the optical filter has a full width at half maximum (FWHM) which is less than approximately 250 nm.

4. The system according to claim 1, wherein the light generated by the radiation source has a spectrum with a bandwidth of at least 500 nm.

5. The system according to claim 1, wherein the light generated by the radiation source has a continuous spectrum.

6. The system according to claim 1, wherein the light generated by the radiation source has a spectrum in the form of a Planck radiator.

7. The system according to claim 1, wherein the detector is a spatially resolving detector.

8. The system according to claim 1, wherein the light generated by the radiation source has a spectrum with at most one maximum intensity value in a spectral range between 1000 nm and 1600 nm.

9. The system according to claim 1, wherein the light generated by the radiation source has a spectrum with the maximum intensity value and the minimum intensity value in a spectral range between approximately 1000 nm and 1600 nm, and the difference between the maximum intensity value and the minimum intensity value in the spectral range corresponds to at most 10% of the maximum intensity value.

10. A method for optical coherence tomography, the method comprising the steps of:
    injecting into an interferometer light emitted by a light source;
    irradiating a sample with light which is emitted by the interferometer; and
    detecting light reflected from the sample with a detector; wherein
    the light emitted by the light source is obtained by filtering spatially incoherent light generated by a radiation source with an optical filter having a bell-shaped or Gaussian spectral filter characteristic;

the filtered light emitted by the light source has a spectrum, a Fourier transform of which has a maximum and one or more secondary maxima a height of which is less than 5% of a height of the maximum; and the light generated by the radiation source has a spectrum with a maximum intensity value and a minimum intensity value, and a difference between the maximum intensity value and the minimum intensity value in a relevant spectral range corresponds to at most 25% of the maximum intensity value.

11. The method according to claim 10, wherein the detector is a spatially resolving detector.

12. A system for optical coherence tomography, the system comprising:
- a light source configured to emit light;
- an interferometer, into which the light emitted by the light source is injected, configured to irradiate a sample with light; and
- a detector configured to detect light reflected from the sample; wherein
- the light source includes a radiation source configured to generate spatially incoherent light and an optical filter having a bell-shaped or Gaussian-shaped spectral filter characteristic configured to filter the light generated by the radiation source;
- the filtered light emitted by the light source has a spectrum, a Fourier transform of which has a maximum and one or more secondary maxima a height of which is less than 5% of a height of the maximum; and
- the light generated by the radiation source is irradiated via a first area, a size of the first area being the same order of magnitude as a size of a second area of the sample irradiated with the light output by the interferometer.

13. The system according to claim 12, wherein the optical filter has a maximum transmittance of light which lies in a spectral range between approximately 1200 nm and 1400 nm.

14. The system according to claim 12, wherein the optical filter has a full width at half maximum (FWHM) which is less than approximately 250 nm.

15. The system according to claim 12, wherein the light generated by the radiation source has a spectrum with a bandwidth of at least 500 nm.

16. The system according to claim 12, wherein the light generated by the radiation source has a continuous spectrum.

17. The system according to claim 12, wherein the light generated by the radiation source has a spectrum in the form of a Planck radiator.

18. The system according to claim 12, wherein the size of the first area and the size of the second area differ from each other by at most 40%.

19. The system according to claim 12, wherein the size of the first area and/or the size of the second area is at least 0.25 mm2.

20. The system according to claim 12, wherein the light generated by the radiation source is irradiated via the first area with a substantially constant intensity.

21. The system according to claim 12, wherein the detector is a spatially resolving detector.

22. The method according to claim 21, wherein the detector is a spatially resolving detector.

23. A method for optical coherence tomography, the method comprising the steps of:
- injecting into an interferometer light emitted by a light source;
- irradiating a sample with light which is emitted by the interferometer; and
- detecting light reflected from the sample with a detector; wherein
- the light emitted by the light source is obtained by filtering spatially incoherent light generated by a radiation source with an optical filter having a bell-shaped or Gaussian spectral filter characteristic;
- the filtered light emitted by the light source has a spectrum, a Fourier transform of which has a maximum and one or more secondary maxima a height of which is less than 5% of a height of the maximum; and
- the light generated by the radiation source is irradiated via a first area, a size of the first area being the same order of magnitude as a size of a second area of the sample irradiated with the light output by the interferometer.

* * * * *